(12) United States Patent
Dassori et al.

(10) Patent No.: US 10,196,333 B2
(45) Date of Patent: Feb. 5, 2019

(54) MULTIPHASE LOW MIXING PROCESSES

(71) Applicant: Archer Daniels Midland Company, Decatur, IL (US)

(72) Inventors: Carlos Gustavo Dassori, Champaign, IL (US); Chi-Cheng Ma, Forsyth, IL (US); Todd Werpy, Decatur, IL (US)

(73) Assignee: Archer Daniels Midland Company, Decatur, IL (US)

(*) Notice: Subject to any disclaimer, the term of this patent is extended or adjusted under 35 U.S.C. 154(b) by 16 days.

(21) Appl. No.: 14/709,591

(22) Filed: May 12, 2015

(65) Prior Publication Data
US 2015/0251980 A1 Sep. 10, 2015

Related U.S. Application Data

(63) Continuation of application No. PCT/US2015/011951, filed on Jan. 20, 2015.

(60) Provisional application No. 61/937,803, filed on Feb. 10, 2014.

(51) Int. Cl.
| | |
|---|---|
| *C07C 29/141* | (2006.01) |
| *B01J 8/04* | (2006.01) |
| *B01J 8/02* | (2006.01) |
| *B01J 38/48* | (2006.01) |
| *B01J 25/04* | (2006.01) |

(52) U.S. Cl.
CPC ............. *C07C 29/141* (2013.01); *B01J 8/025* (2013.01); *B01J 8/0242* (2013.01); *B01J 8/0278* (2013.01); *B01J 8/0457* (2013.01); *B01J 8/0492* (2013.01); *B01J 25/04* (2013.01); *B01J 38/48* (2013.01); *B01J 2208/00212* (2013.01)

(58) Field of Classification Search
CPC ....... C07C 29/141; B01J 8/0492; B01J 8/025; B01J 2208/00212
USPC .......................................... 568/863; 536/124
See application file for complete search history.

(56) References Cited

U.S. PATENT DOCUMENTS

| | | | |
|---|---|---|---|
| 3,144,404 A * | 8/1964 | Tyson | B01J 8/02 208/110 |
| 3,425,810 A | 2/1969 | Scott, Jr. | |
| 3,489,674 A | 1/1970 | Borts, Jr. | |
| 3,728,249 A | 4/1973 | Antezana et al. | |
| 4,322,569 A * | 3/1982 | Chao | C07C 31/26 568/863 |
| 4,985,134 A | 1/1991 | Derr, Jr. et al. | |
| 5,290,427 A | 3/1994 | Fletcher et al. | |
| 5,492,617 A | 2/1996 | Trimble et al. | |
| 5,603,824 A | 2/1997 | Kyan et al. | |
| 6,299,759 B1 | 10/2001 | Bradway et al. | |
| 6,583,186 B2 | 6/2003 | Moore, Jr. | |
| 8,197,559 B2 | 6/2012 | Abe et al. | |
| 2003/0010678 A1 | 1/2003 | Kalnes | |

* cited by examiner

*Primary Examiner* — Yih-Horng Shiao
(74) *Attorney, Agent, or Firm* — William B. Miller

(57) ABSTRACT

A process is described for improving the performance of certain multiphase reaction systems including a solid catalyst, one or more reactants in the gas phase and one or more reactants in the liquid phase, wherein a targeted maximum concentration of a reactant in the liquid phase is identified for providing improved value in terms of byproduct formation, catalyst deactivation and yields of desired products, and this targeted concentration is closely approached and preferably achieved, but not substantially exceeded, downstream in a continuous process or later in time from the initiation of a batch in a semibatch mode of operation of such processes.

20 Claims, 3 Drawing Sheets

MULTIPHASE LOW MIXING PROCESSES

CROSS REFERENCE TO RELATED APPLICATIONS

This application is a continuation from Patent Cooperation Treaty Application No. PCT/US15/11951 filed Jan. 20, 2015, which in turn claimed the benefit of U.S. Ser. No. 61/937,803 filed Feb. 10, 2014.

TECHNICAL FIELD

The present invention relates generally to chemical processes including one or more reactants in the gas phase, one or more reactants in the liquid phase and a solid catalyst, and more particularly relates to those multiphase processes that are characterized as low mixing—i.e., exhibiting plug flow or quasi-plug flow of the reactants (an optionally of the catalyst, for example, a transported bed) in a continuous mode of operation or a semi-batch mode of operation.

BACKGROUND OF THE INVENTION

Multiphase processes involving the reaction of gas and liquid phase reactants on a solid catalyst form the basis for production of a large variety of intermediate and end products, as examples, in the manufacture of monomers and pharmaceuticals and in crude oil processing. From the perspective of the gases used in such processes, a number of commercially important gas-liquid reaction systems can be considered for instance that involve the reaction of hydrogen with a liquid substrate (hydrogenation, hydrogenolysis, hydrotreating), that involve the reaction of oxygen or a similar oxygen-based gaseous reactant (e.g., ozone) with a liquid substrate (oxidation, ozonolysis), that involve the reaction of a halogen gas with a liquid substrate (fluorination, chlorination) or that involve the use of a combination of gases (hydroformylation).

Solid catalysts are desirably used in both gas-liquid and in liquid-liquid reaction systems for facilitating the separation and recovery of spent catalyst and the processing of crude reaction products, but gas-liquid reaction systems frequently pose difficulties in terms of getting a gaseous reactant into a liquid and to a heterogeneous solid catalyst surface. As a result, in certain types of multiphase processes particularly (as elaborated in greater detail hereafter), substoichiometric gas to liquid reactant ratios can occur in the presence of the catalyst, so that undesirable side reactions can be catalyzed of liquid phase components at the solid catalyst interface. As well, replenishment of the gas reactant(s) is difficult as the gas reactant(s) is spent in these undesirable side reactions. Further, catalyst lifetime can be shortened by the interaction of the liquid reactant(s) with the catalyst.

The relative overabundance of a liquid reactant as compared to a gaseous reactant (which can be an alternative way of considering a substoichiometric gas to liquid reactant ratio condition) can particularly be an issue with those continuous reaction systems that are characterized by limited axial mixing from inlet to outlet, i.e., that are plug flow or quasi-plug flow in nature, as intrinsically a liquid substrate concentration is high at the inlet and lower at the outlet of the reactor, as well as in semibatch reaction systems, since again intrinsically a liquid substrate concentration is greatest at the start of a batch and lower at the end.

These and other complexities and difficulties of carrying out multiphase processes involving a solid catalyst and gas and liquid phase reactants are well documented in the literature and well-known to those in the art. In *Trickle Bed Reactors: Reactor Engineering & Applications*, V. V. Ranade, R. V. Chaudhari and P. R. Gunjal, Elsevier, Amsterdam (2011), for example, the advantages and disadvantages of various multiphase reactor systems are discussed at pages 9-12, including slurry reactors (where the reaction is carried out between mobile catalyst particles, gas, and liquid phases) and fixed-bed reactors (where the reaction between gas and liquid phase reactants takes place on or at the stationary catalyst).

In contrast, well-mixed slurry reactors (whether operated continuously or, as is more common, in a batchwise manner) facilitate effective temperature control within the reactor and are characterized by intensive mass transfer between all phases. However, as discussed in the cited reference, such well-mixed slurry reactors pose difficulties in terms of the separation of the product from the catalyst due to catalyst attrition, in terms of abrasion of equipment surfaces by moving catalyst particles, in terms of low specific productivity per unit volume, and in terms of use in a continuous mode taking into account catalyst separation and regeneration needs.

Accordingly, fixed bed reactors have been viewed as favored especially for continuous processes, however, these reactors have their own limitations, complexities and disadvantages in the context of carrying out multiphase processes involving reactants in the gas and liquid phases and a solid catalyst.

The substoichiometric issues described above are among the limitations, complexities and disadvantages recognized and discussed in a general frame of reference in Datsevich et al., "Multiphase fixed-bed technologies: Comparative analysis of industrial processes (experience of development and industrial implementation)", Applied Catalysis A: General, vol. 261, pp 143-161 (2004) (hereinafter "Datsevich"), in particular on page 148 and following in relation especially to FIG. 4, wherein Datsevitch observes that in the initial part of a multiphase fixed bed reactor wherein the gas and liquid phase reactants first combine there is a significant stoichiometric excess of the liquid reactant both in the bulk liquid as well as at the catalyst surface, so that the reaction in this initial part is limited by mass transport resistance of the gas into the liquid (especially for gases such as hydrogen and oxygen having "very bad solubility in liquids"). At the same time, in the latter part of the reactor, Datsevich observes that these systems are mass-transfer-limited by the liquid compound. Datsevich also observes that along the axial flow of a fixed bed multiphase gas-liquid reaction system there is a point at which there is an "ideal" correlation of the concentrations of the gas and liquid reactants, wherein the concentration of a liquid phase reactant corresponds to the stoichiometric concentration of a gaseous reactant on the catalyst surface, so that for active catalysts both concentrations are zero at the catalyst surface.

The complexities of carrying out these multiphase processes in a continuous fixed bed reactor are explored experimentally and through math modeling in a more specific context of interest for the present invention in a preferred application, in Kilpio et al., "Experimental and Modeling Study of Catalytic Hydrogenation of Glucose to Sorbitol in a Continuously Operating Packed-Bed Reactor", Ind. Eng. Chem. Res. 2013, vol. 52, pp 7690-7703, wherein temperature- and concentration-dependent reaction kinetics, catalyst deactivation, internal diffusion and heat conduction within the solid catalyst particles, radial heat conduction and mass dispersion in a selected reactor section, liquid holdup, gas-liquid mass transfer, pressure drop and axial dispersion were evaluated in, and used to math-model, a lab scale (1.15 cm diameter, 7 cm long) continuous flow packed bed reactor containing 0.5 grams of a commercial ruthenium on carbon catalyst.

In recognition of the above-mentioned complexities and mass transfer related limitations of continuous fixed bed multiphase reaction systems, continual efforts have been made to improve the performance of such systems.

Datsevich proposes one refinement to address and reduce mass transfer limitations from gas to liquid, using instead a "saturator" before the reactor to accomplish the mass transfer, so that only a liquid phase saturated with gas is fed into the reactor. In effect, the reactor volume in the initial part of a fixed bed reactor holding the gas phase is avoided altogether. Datsevich observes that since the solubilities of gases such as hydrogen and oxygen are low and the concentration of the liquid reactant in the feed is comparatively higher than the equilibrium gas concentration in the liquid phase, recycling of the final product through the saturator is necessary to deliver the needed quantity of gas to the reaction zone. Datsevich thus effectively takes the approach of diluting the inlet or starting concentration of a substrate in the liquid phase (using the product or a portion thereof as the diluent), so limiting the liquid substrate's availability to the heterogeneous catalyst in a corresponding way as a gaseous reactant's availability to the catalyst is limited by gas solubility and resistance to mass transfer considerations.

A series of published applications and issued patents to Michael D. Ackerson and others, see, e.g., US 2012/0184789 to Ackerson et al.; U.S. Pat. No. 7,569,136; U.S. Pat. No. 7,291,257; U.S. Pat. No. 6,881,326; U.S. Pat. No. 6,428,686; and U.S. Pat. No. 6,123,835, are of a very similar nature, wherein various methods of hydroprocessing both petroleum and non-petroleum feedstocks (US 2012/0184789) are described in which a diluent is fed with hydrogen and a feedstock in need of hydroprocessing so that substantially all of the feed and hydrogen are in a single, continuous liquid phase as a hydrogen-gas-free liquid feed stream to the reactor. As in Datsevich, the diluent can be at least a portion of a cooled and/or separated reaction product that is recycled.

In effect, both Datsevitch's presaturated one-liquid-flow (or POLF) technology and Ackerson's process technology operate in the liquid mass transfer-limited region of FIG. 4 in Datsevitch, and use dilution and significant product recycling to cope with throughput decay while avoiding the substoichiometric issues in the initial part of the reactor in a conventional fixed bed multiphase reaction system that have been mentioned above. However, these types of approaches do intrinsically involve some loss of productivity in the use of dilution, as well as significant costs for the substantial recycle that is required especially for low-solubility gases such as hydrogen and oxygen.

Because of this recycle aspect of Datsevich's and Ackerson's approaches, these approaches have however been recognized as ill-suited for chemical processes involving high rates of gas consumption in that enormous product recycle rates (or equivalent dilution, diluent recovery and recycle for non-product diluents) would be required. Modifications of the POLF concept have accordingly been proposed wherein some gas would enter the reactor in the gas phase so that as gas in the liquid phase in consumed by reaction, a constant gas concentration in the liquid phase would be maintained through the whole of the fixed bed, see, e.g., DE 102006044579, RU 2083540 and WO 03091363.

Another approach to the particular substoichiometric issues described above would be to improve the solubility and/or availability of gas phase reactants in the liquid phase. Though not in regard to a process involving a solid catalyst, US 2013/0240781 A1 to Subramaniam et al., for example, reports a method for increasing the ozone concentration in a liquid, and then using the increased ozone concentration liquid for performing (in the absence of a catalyst) ozonolysis of a substrate. As related by Subramaniam et al., ozonolysis has typically been performed by bubbling ozone through an aqueous phase or through an organic liquid phase containing a substrate. However, these traditional methods are described as having certain drawbacks. Since ozone is highly reactive, the reaction temperature must be subambient (close to 0 degrees Celsius), but ozone is of limited solubility in a liquid phase at these temperatures. Further, ozone tends to react with many traditional organic solvents that might be used, resulting in waste products and further limiting ozone availability for conducting the reaction. The solution offered by Subramaniam et al. is to introduce ozone into an inert liquid under circumstances wherein the ozone/liquid combination has a temperature between about 0.8 and 1.5 times the critical temperature of ozone, and increasing isothermally the pressure of the ozone-containing gas above the liquid to about 0.3 to about 5 times the critical pressure of ozone so as to increase the solubility of the ozone in the liquid. The pressure is controlled to tune the solubility of the ozone in the liquid.

U.S. Pat. No. 7,365,234 by Subramaniam et al. adopts a similar approach in the context of the catalytic hydroformylation of olefinic feedstocks, wherein an olefin is reacted with CO and $H_2$ in the presence of a hydroformylation catalyst in a liquid that has been volumetrically expanded with a compressed gas, typically supercritical or subcritical (near critical) carbon dioxide added generally to the limits of the solubility of a homogeneous Rh-based catalyst, to tunably increase the amount of CO and $H_2$ available for reaction in the liquid phase. Surprisingly, altering the amount of the compressed gas in the liquid phase alters the chemoselectivity of the products, and varying the content of the compressed gas in the liquid allows higher ratios of the more desired linear aldehyde to less desired branched aldehyde products to be realized.

In hydroprocessing, too, processes are known wherein a hydrogen donor solvent or another material is used to improve hydrogen transfer and availability into the reacting liquid phase, however, at the cost of requiring additional separation and recovery/recycle steps, or in relation to the Subramaniam references with the requirement of operating under certain near critical ranges of conditions with the added costs associated with achieving and maintaining these conditions.

SUMMARY OF THE INVENTION

The present invention in one aspect relates to a process for improving multiphase, low mixing reaction systems including a solid catalyst, one or more reactants in the gas phase and one or more reactants in the liquid phase, by closely approaching and preferably achieving, but not substantially exceeding, both initially and downstream in a continuous process (or later, in a semibatch process), a targeted concentration of a liquid phase reactant. The targeted concentration will in preferred embodiments correspond to that concentration that provides maximum economic value in the context of a particular continuous, multiphase low mixing reaction system over a reference timeframe, considering catalyst deactivation rates, byproduct formation and related purification requirements, productivity in terms of desired products and selectivity to those products and so forth.

In effect, the present invention according to this aspect seeks to not only achieve but perpetuate along at least some portion of the length (meaning, in the axial flow direction to the product outlet) of a multiphase low mixing gas-liquid reaction system, or for a longer period of time in a semibatch, multiphase low mixing process, an initial concentration of a liquid reactant at the start of a continuous plug flow or quasi-plug flow process or at the start of a semibatch process that provides a desired performance of the overall reaction system under selected and preferably optimized operating conditions.

From another perspective, the present invention seeks to avoid or at least reduce the occurrence of significantly substoichiometric ratios of a gaseous reactant to a liquid substrate with which the gaseous reactant is to react over the length of a continuous reactor (from the initial combining of the gaseous reactant and the liquid substrate to the product outlet) or over the duration of a semibatch reaction through controlling the liquid substrate concentration, without requiring a dilution of the liquid substrate entering the reactor or at the beginning of a batch.

In one embodiment of a continuous process, this is accomplished by introducing a liquid phase reactant into the reactor at the targeted concentration of the liquid phase reactant at a plurality of locations in the direction of fluid flow through the reactor toward the product outlet. In a variation, a gaseous feed is introduced at one or more locations downstream of the inlet to maintain a desired gas/liquid ratio in the reactor. It is expected that the multiphase continuous process will most commonly be carried out in a fixed bed reactor of the trickle bed or packed bubble column variety or in a series of such reactors including quench boxes wherein downstream additions of the liquid phase reactant will be accomplished, though continuous multiphase, low mixing slurry reactors (transported bed reactors) are contemplated as well.

In another embodiment of a continuous process, a liquid phase reactant is introduced at the inlet in the targeted concentration, and at one or more downstream locations in a concentration or concentrations greater than the targeted concentration, as needed to closely approach and preferably achieve, but not substantially exceed, the targeted concentration in the reactor from the addition point. In a variation, a gaseous feed is introduced at one or more locations downstream of the inlet to maintain a desired gas/liquid ratio in the reactor. Again, it is expected that most commonly such continuous multiphase processes will be carried out in a fixed bed reactor of the trickle bed or packed bubble column variety or in a series of such reactors, but other continuous low mixing embodiments are contemplated.

In a further variation of either of these embodiments, namely, wherein the downstream addition or additions are at a targeted concentration of a reactant in the liquid phase or at a concentration or concentrations greater than the targeted concentration, the number of downstream additions and their placement relative to where the gas and liquid reactants are first combined in the presence of the catalyst and reacted are selected so as to minimize the total catalyst requirements for a certain production rate of a desired product, or at least to enable a substantial reduction in total catalyst requirements compared to a scenario wherein no downstream additions are made. In certain embodiments, the requisite configuration (in terms of number of additions and placement thereof) for minimizing or at least accomplishing a significant reduction in the total catalyst requirements is accomplished iteratively by experimentation. In other embodiments, the requisite configuration is determined by a process including modeling the performance of the system as a function of the number and placement of downstream additions of a liquid phase reactant at the targeted concentration or at a greater concentration or concentrations.

In one embodiment of a semibatch process, a liquid phase reactant is introduced at the targeted concentration at the initiation of a batch, and one or more additions of the liquid phase reactant are later made each at the targeted or a greater concentration than the first concentration, as needed to closely approach and preferably achieve, but not substantially exceed, the targeted concentration in the reactor from the time of an addition. In a variation, one or more additions of a gaseous feed are made after the initiation of a batch to maintain a desired gas/liquid ratio in the batch.

In a further variation of either of these semibatch embodiments, namely, wherein the later addition or additions are at a targeted concentration of a reactant in the liquid phase or at a concentration or concentrations greater than the targeted concentration, the number of additions and their timing relative to the initiation of a batch are selected so as to minimize the total catalyst requirements for a certain production rate of a desired product or at least to enable a substantial reduction in total catalyst requirements compared to a scenario wherein no later additions are made. In certain embodiments, the requisite configuration (in terms of number of additions and timing thereof) for minimizing or at least accomplishing a significant reduction in the total catalyst requirements is accomplished iteratively by experimentation. In other embodiments, the requisite configuration is determined by a process including modeling the performance of the system as a function of the number and timing of later additions of a liquid phase reactant at the targeted concentration or at a greater concentration or concentrations.

The principles involved in the process of the present invention and the manner in which the present invention can be utilized to provide improved process economics in these multiphase gas-liquid reaction systems will be more readily understood on considering the following drawings and detailed description of certain embodiments of the invention, which will be understood as not limiting of the scope of the present invention and as provided for purposes of illustration only.

DESCRIPTION OF ILLUSTRATIVE EMBODIMENTS OF THE INVENTION

Figure 1:
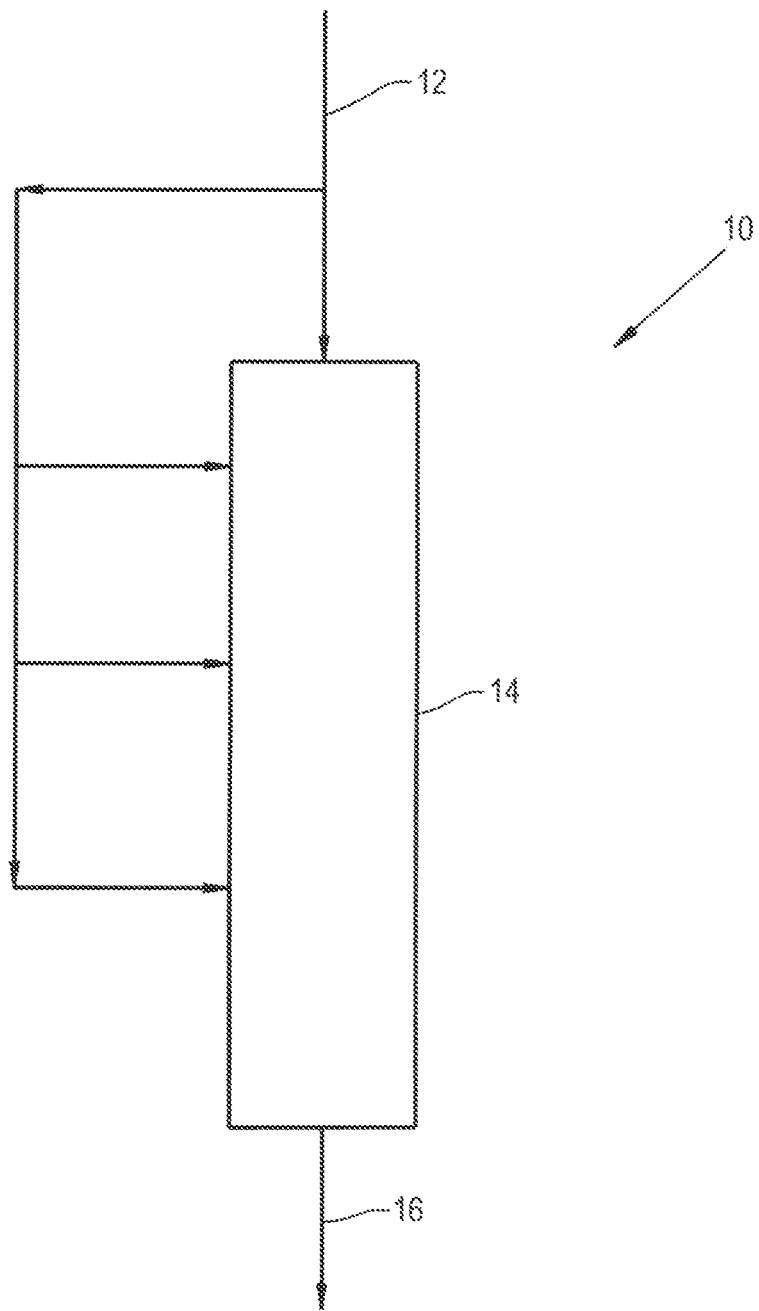
FIG. 1 is a schematic representation of a continuous multiphase process embodiment of the present invention.

A number of processes have been mentioned above, in which the present invention may be beneficially employed. Those skilled in the art will understand that these processes and especially the specific example embodiments described in greater detail hereafter are not however to be considered limiting of the present invention, and that the present invention can be of value generally for multiphase, low mixing processes involving a solid catalyst and reactants in both the gas and liquid phases, wherein gas solubility and gas-liquid mass transfer limitations may result in substoichiometric gas-liquid reactant ratios and to such difficulties as throughput limitations, byproduct formation and side reactions, and catalyst deactivation. The present invention is also expected to be of significant value generally in the context of such multiphase phases which are further characterized by higher consumption rates of a gaseous reactant, for example, in applications wherein the saturated, single liquid approach of Datsevich or Ackerson et al. would require an impracticably large recycle.

This having been said, it is considered that one desirable application of the present invention will be for improving processes in which hydrogen gas reacts with a substrate in a liquid, e.g., in hydrogenation, hydrogenolysis and hydrotreatment, and especially but without limitation for improving those solid-catalyzed processes in which hydrogen gas reacts with a substrate in a liquid.

An example of a commercially significant hydrogenation is the hydrogenation of sugars to sugar alcohols, for example, dextrose to sorbitol. Conventionally an aqueous sugars solution is hydrogenated, and there are numerous published examples of different catalysts and associated process conditions for carrying out this transformation.

GB 806,236 (1957) describes the known use of platinum, palladium and nickel catalysts, but indicates that none of these exhibited highly efficient conversions at reaction temperatures below 160 degrees Celsius and hydrogenation pressures below 1500 psig, whereas the claimed supported ruthenium or ruthenium-based catalyst was prescribed for use at hydrogenation pressures ranging from 100 to 1500 psig and temperatures of preferably 80 to 200 degrees Celsius. Examples are given of the hydrogenation of dextrose, sucrose, maltose and lactose.

GB 1,025,813 (1966) concerns a process for producing mannitol, sorbitol and mixtures of these by the catalytic hydrogenation of an aqueous solution (20 to 80 percent by weight) of dextrose and/or invert sugar in the presence of lime (CaO) and a supported nickel catalyst, at hydrogenation pressures of from 500 to 3000 psig and a temperature of from 60 to 100 degrees Celsius.

U.S. Pat. No. 4,292,451 to deBerardinis et al. (1981) describes the catalytic hydrogenation of an aqueous solution of dextrose and mannose in the presence of preferably a supported nickel catalyst, wherein the sugars mixture contains a mannitol yield-enhancing amount of an alkali metal salt of a weak acid, for example, sodium carbonate. Preferably the hydrogenation is done in two stages, with the first conducted at from 80-95 degrees Celsius, and the second at 120-150 degrees Celsius.

EP 0 006 313 (1982) describes a number of known hydrogenation methods for reducing sugars to sugar alcohols, but suggests the majority are not stereoselective. The claimed advance in EP'313 is a method for reducing a sugar to a particular stereoisomer in significant excess and preferably exclusively, using a supported catalyst of finely divided metallic copper and a particulate support material. The sugar is brought into contact with the catalyst in the presence of a solvent medium. Organic solvents are mentioned as possibilities, but hydrophilic solvents are preferred, and water is most preferred.

A literature survey produces a number of catalysts of a similar character for hydrogenating dextrose solutions to produce sorbitol: ruthenium on carbon; a supported Ni catalyst including Co, Mn, Cu, Cr, Mo, Ca, Zn, Fe or W; an amorphous NiMoAl catalyst; a Raney® nickel sponge metal catalyst modified by molybdenum; nickel and/or cobalt plated sponge catalysts; Mo-, Cr- and Fe-promoted Raney® nickel sponge metal catalyst catalysts and so forth.

While certain of the references mention limiting the concentration of sugars in the feed to avoid handling difficulties from the feed being too viscous (U.S. Pat. No. 4,292,451) or sugars crystallizing out of solution (GB 1,025,813) or suggest performing the hydrogenation in stages at different operating conditions (U.S. Pat. No. 4,292,451), and while all obviously seek improvements in the yield of the desired sugar alcohol product(s) from adopting a new catalyst or modification of an existing catalyst, none of these processes suggests feeding a portion of the sugars solution into contact with the prescribed catalyst at a targeted substrate concentration at a plurality of locations in the direction of fluid flow through the reactor in a continuous process (or at the targeted concentration at the reactor inlet and at a greater concentration downstream of the inlet to approach, but not substantially exceed the targeted concentration downstream of the inlet), or at different times in a semibatch process. Nevertheless, based on the results we have obtained as described in the examples below, it is considered that all of the various known catalysts, additives and methods for hydrogenating sugars to sugar alcohols, for instance, can be beneficially adapted according to the present invention.

Referring now to FIG. 1, a schematic illustration is provided of a continuous multiphase process embodiment of the present invention. In the context of a process 10 for the hydrogenation of one or more sugars in an aqueous solution, a combined hydrogen and aqueous sugar(s) solution feed 12 at a selected sugar (substrate) concentration is fed to a reactor 14 containing a suitable hydrogenation catalyst. The aqueous sugar(s) solution feed 12 is also introduced at one or more additional locations downstream of where the solution 12 is first fed into the reactor 14, at appropriate flow rates so as to closely approach and preferably achieve, but not substantially exceed, a concentration of sugar in the liquid phase in the reactor 14 equal to that of the feed 12. In a variation that may be particularly relevant for high gas consumption systems, additional hydrogen (or a gas reactant in a generalized embodiment) may be input to the reactor 14 at one or more additional locations beyond the inlet. As a result of the one or more downstream additions of solution 12, preferably a sugar concentration that is within thirty percent of the selected concentration in solution 12 is realized for at least about ten percent of the reactor 14's length, and more preferably for at least about thirty percent of the reactor 14's length.

A product stream 16 is then recovered from the reactor 14, and sent on for further processing and purification (not shown) as needed and as is conventionally known.

The substrate concentration in feed 12 (and targeted in the reactor 14 downstream of the inlet, through the further addition points) will be designed in certain preferred embodiments to maximize (or certainly at least improve) the economic value derived at a given point in time from the production of the desired product(s) from a given gas/liquid reaction system.

Typically in this regard there will be an optimal gas/liquid reactant feed ratio (and correspondingly an optimal substrate concentration in the liquid feed) for a given gas/liquid process that will balance expected side reactions in the liquid phase as well as catalyst deactivation/degradation due to substoichiometric gas/liquid reactant conditions prevailing in the reactor (in light of the abovementioned solubility and gas/liquid mass transfer constraints) against added liquid reactant throughput, and the process of the present invention in preferred embodiments seeks by means of subsequent additions of a liquid reactant or substrate (and of gaseous reactant as needed) to closely approach or preferably realize these optimal conditions over at least a greater portion of the length of a continuous reactor, or for a longer period of time in the course of a semibatch process, than occurs in the absence of the subsequent additions. By utilizing accumulated product as a co-solvent, the additional solvent separation and recovery costs and the throughput losses from the substrate dilution that would be required of a single feed to avoid significantly substoichiometric conditions and attendant byproduct formation and catalyst degradation/deactivation difficulties can additionally be avoided. In a continuous process, these substrate additions occur at one or more different, side injection points along the axial flow from reactor inlet to outlet, while in a semibatch process these substrate additions will occur in one or more instances over the duration of a batch from start to completion.

As will be demonstrated by the examples below and as will be discussed more fully below, by operating in this manner a number of benefits can be obtained. One significant benefit is that the manufacturer can substantially reduce the volume of catalyst required in its process to produce a given amount of a desired product. In the dextrose to sorbitol process that is specifically addressed in the examples, the Raney® nickel sponge metal catalyst that was used as of the time of filing cost about $30/lb, so a reduction in the total catalyst volume required of at least 10 percent, at least 20 percent and at least 30 percent will represent a substantial savings.

Parenthetically, by "side injection" or any similar terminology used herein it is not intended that a particular manner of addition is required, and such terms should be understood as encompassing any manner by which an additional supply of a reactant (liquid or gas) may be introduced into a continuous multiphase process downstream of the point at which the gas and liquid reactants are combined in the presence of a solid catalyst and the reaction is initiated, or at a later time from the initiation of a batch in a semibatch mode of operation.

It will be immediately appreciated given the variety of gas/liquid reaction systems generally and given the numerous catalyst systems, ranges of operating conditions and other process refinements suggested for carrying out a given gas/liquid reaction, as illustrated above, for example, in the hydrogenation of sugars to sugar alcohols—not to mention changes in market conditions affecting the value of products and the various costs that affect the value proposition for operating a process in a certain way at a point in time—that it is not realistically possible to specify what selected substrate concentration would be "best" for every solid-catalyzed gas/liquid reaction system to which the present invention can be beneficially applied—but those skilled in the art will be well able with an understanding of the principles behind the present invention and in light of the illustrative examples that follow (as well as previous work with a particular gas/liquid reaction system at various substrate concentrations) to determine and select a substrate concentration to achieve in the initial feed to a reactor and to target for approaching in the reactor through subsequent substrate additions.

In certain embodiments according to either a continuous or a semibatch mode of operation, as previously mentioned and as demonstrated by the examples that follow, the number of additions of a reactant (gas and/or liquid) and the placement or timing of each of those additions for achieving a targeted concentration of a liquid phase reactant (whatever that may be) can be selected to maximize a reduction in the total catalyst requirements to produce a certain amount of a desired product within a given time in a continuous process or per batch in a semibatch process. For the same reasons given above, it is not realistically possible either to specify in advance how many additions should be made or where or when each addition should be made, however, those skilled in the art should be well able to determine the number and placement or timing of additions of a reactant that should be used to reduce total catalyst requirements by a desired amount or to minimize the total catalyst requirements for a given reaction system. In some instances, this determination may most conveniently be made iteratively by experimentation, as for example where a single downstream or later addition is contemplated in a given process, while in other instances the most reasonable way to proceed will be to construct or employ a computer model of the reaction system's performance as a function of the number and placement or timing of additions. The number and placement or timing of additions can then be validated in many instances, as needed, in a pilot scale unit before modifying an existing commercial scale reactor or series of reactors or before constructing apparatus to accomplish the indicated number of additions where and/or when indicated.

Figure 2:
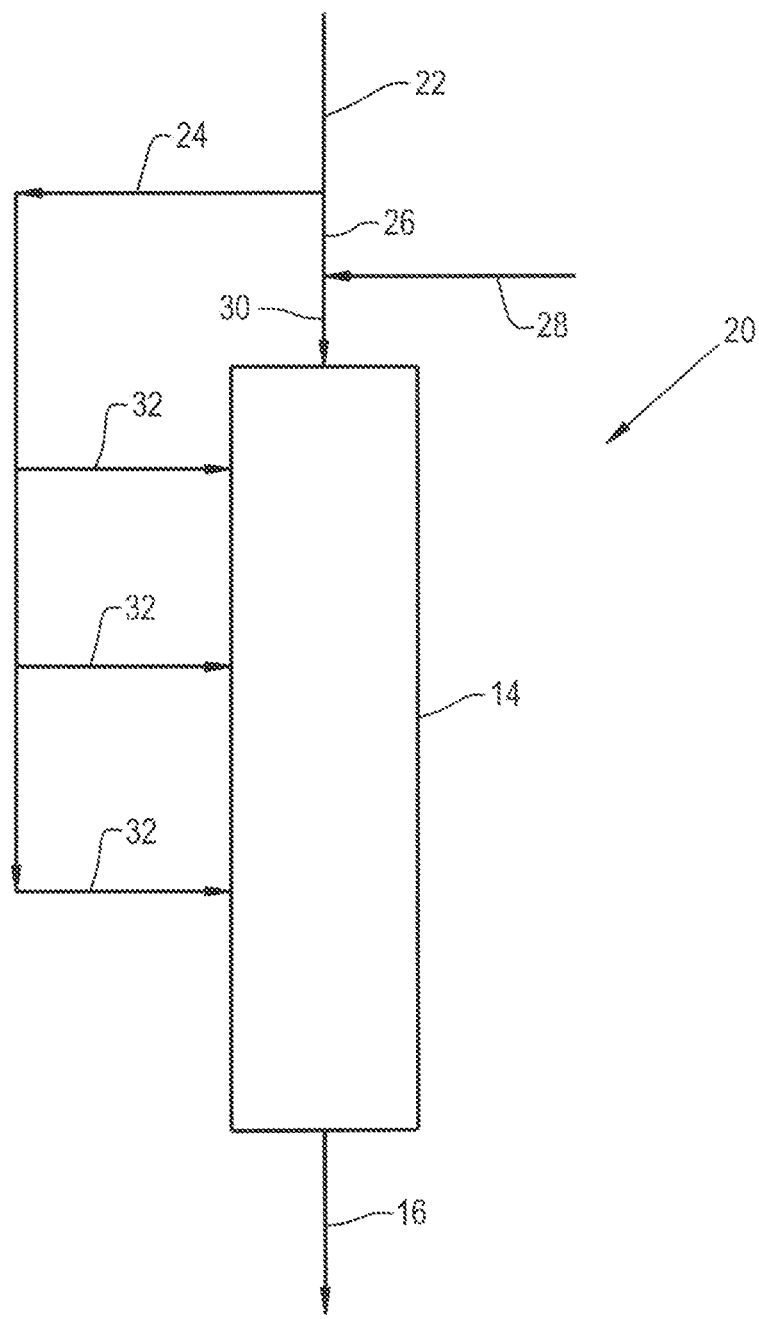
FIG. 2 is a schematic representation of an alternative continuous multiphase process embodiment of the present invention.

Because the targeted concentration of a liquid phase reactant for greatest value realization can be expected to vary somewhat over time, it is considered that an embodiment as schematically illustrated in FIG. 2 will be generally preferred for practicing the present invention. Turning now to FIG. 2, in the particular illustrative context of hydrogenating an aqueous sugar solution, such as hydrogenating an aqueous dextrose solution to provide sorbitol, an embodiment 20 is shown in which a concentrated aqueous dextrose solution 22 is divided into a downstream injection portion 24 and a feed portion 26. The concentrated aqueous dextrose solution 22 has a higher concentration than the targeted concentration in the reactor 14. The feed portion 26 is diluted with additional water 28 to achieve an aqueous inlet feed 30 at the targeted dextrose concentration, while downstream injection portion 24 is used to introduce one or more downstream portions 32 of the more concentrated aqueous dextrose solution 22 into the reactor 14. By using a more concentrated solution 22 and diluting with additional solvent 28 to reach a targeted inlet concentration of a reactant in the liquid phase, refinements in the targeted inlet concentration responsive to the use of a different catalyst, for example, may be quickly and easily made.

As mentioned, what concentration should be targeted for any given multiphase system will depend on a number of factors, including but not being limited to what catalyst is used and how that catalyst tends to lose activity at various inlet concentrations in that gas/liquid system. In the particular context of a process for producing sorbitol by the continuous hydrogenation of an aqueous solution of dextrose with a Raney® nickel sponge metal catalyst, however, we found as demonstrated by the examples below that material improvements in the productivity and longevity of the catalyst were able to be realized by selecting a dextrose concentration in the aqueous feed of not more than about 30 percent, preferably not more than about 25 percent, and more preferably about 20 percent or less, and carrying out at least one and preferably more than one side injection of a concentrated dextrose solution to realize the targeted feed concentration in the reactor downstream of the inlet.

Another commercially important example of a process wherein hydrogen is reacted with a substrate in the liquid phase is the hydrogenolysis of C—O and C—C bonds, especially of sugars, sugar alcohols, lactic acid and glycerol in solutions of the same to produce various desired chemical products, such as propylene glycol.

U.S. Pat. No. 6,841,085 to Werpy et al. in this regard describes a number of known processes of this character, wherein an aqueous solution of saccharose was converted by hydrogenolysis over a nickel-on-kieselguhr catalyst to a product containing glycerol and propylene glycol (or 1,2-propanediol) (see U.S. Pat. No. 3,030,429 to Conradin et al), sorbitol was converted by hydrogenolysis to glycerol over the same catalyst with an alkali promoter being added to the feedstream to control pH and nickel leaching (U.S. Pat. No. 4,338,472 to Sirkar), hydrogenolysis of sorbitol and xylitol over a nickel on silica/alumina catalyst produced ethylene glycol, propylene glycol and glycerol (U.S. Pat. No. 4,404,411 to Tanikella), and sorbitol was converted again to propylene glycol over a ruthenium-on-carbon catalyst (U.S. Pat. No. 5,600,028 to Gubitosa). In the Werpy '085 patent, sorbitol, glycerol, xylitol and lactic acid examples are given over a Re-containing multimetallic catalyst wherein ethylene glycol, glycerol or propylene glycol or any combination thereof are produced, with particular emphasis on the production of propylene glycol.

Still another example of a gas-liquid reaction system in which the process of the present invention may be applied is in the heterogeneously catalyzed hydrotreatment of hydrocarbons in a petroleum refining context. Hydrotreating or hydroprocessing refers to a variety of catalytic hydrogenation processes which saturate unsaturated hydrocarbons and remove S, N, O and metals from different petroleum streams in a refinery. These contaminants, if not removed from the petroleum fractions as they travel through the refinery processing units, can have detrimental effects on the equipment, the catalysts, and the quality of the finished product.

Typically, hydrotreating is done prior to processes such as catalytic reforming so that the reforming catalyst is not contaminated by untreated feedstock. Hydrotreating is also used prior to catalytic cracking to reduce sulfur and improve product yields, and to upgrade middle-distillate petroleum fractions into finished kerosene, diesel fuel, and heating fuel oils. In addition, hydrotreating converts olefins and aromatics to saturated compounds.

Hydrotreating processes represent some of the most important catalytic processes and the annual sales of hydrotreating catalysts represent close to 10% of the total world market for catalysts.

Hydrotreating for sulfur removal is called hydrodesulfurization. In a typical catalytic hydrodesulfurization unit, the feedstock is deaerated and mixed with hydrogen, preheated in a fired heater (600°-800° F.) and then charged under pressure (up to 1,000 psi) through a fixed-bed catalytic reactor. In the reactor, the sulfur and nitrogen compounds in the feedstock are converted into hydrogen sulfide ($H_2S$) and ammonia ($NH_3$). The reaction products leave the reactor and after cooling to a low temperature enter a liquid/gas separator. The hydrogen-rich gas from the high-pressure separation is recycled to combine with the feedstock, and the low-pressure gas stream, rich in $H_2S$, is sent to a gas treating unit where $H_2S$ is removed. The clean gas is then suitable as fuel for the refinery furnaces. The liquid stream is the product from hydrotreating and is normally sent to a stripping column for removal of $H_2S$ and other undesirable components. In cases where steam is used for stripping, the product is sent to a vacuum drier for removal of water. Hydrodesulfurized products are blended or used as catalytic reforming feedstock.

Other hydrotreating applications in which the process of the present invention may be used include using hydrotreating to improve the burning characteristics of distillates such as kerosene, by converting aromatics into naphthenes, which are cleaner-burning compounds. Lube-oil hydrotreating uses catalytic treatment of the oil with hydrogen to improve product quality. The objectives in mild lube hydrotreating include saturation of olefins and improvements in color, odor, and acid nature of the oil. Mild lube hydrotreating also may be used following solvent processing. Operating temperatures are usually below 600° F. and operating pressures below 800 psi. Severe lube hydrotreating, at temperatures in the 600°-750° F. range and hydrogen pressures up to 3,000 psi, is capable of saturating aromatic rings, along with sulfur and nitrogen removal, to impart specific properties not achieved at mild conditions.

The process of the present invention may also be used in the hydrotreating of pyrolysis gasoline (pygas), a by-product from the manufacture of ethylene. Traditionally, the outlet for pygas has been motor gasoline blending, a suitable route in view of its high octane number. However, only small portions can be blended untreated owing to the unacceptable odor, color, and gum-forming tendencies of this material. The quality of pygas, which is high in diolefin content, can be satisfactorily improved by hydrotreating, whereby conversion of diolefins into mono-olefins provides an acceptable product for motor gas blending.

Against the backdrop of these several hydrotreating examples those familiar with the petroleum refining and upgrading arts will readily appreciate from a still broader perspective, given the numerous ways in which hydrogen is used or has been known to be useful in petroleum refining and upgrading, that a number of heterogeneously catalyzed gas-liquid reaction systems and operations involving hydrogen as a reactant are known in the context of petroleum refining and upgrading and could also make use of the process of the present invention.

The present invention is further demonstrated by the non-limiting examples that follow:

Example 1

Monohydrate dextrose solution (50 percent dissolved solids) was diluted with water to provide a 20% concentration aqueous dextrose feed (used for Example 2 below) and a 30% concentration aqueous dextrose feed (used for this Example 1). Soda ash was added to each feed to adjust to a pH of 7.2.

A 30 cubic centimeter fixed-bed stainless steel reactor having an internal diameter (ID) of 0.24 cm (0.61 inches) was loaded with a commercial Raney® nickel sponge metal catalyst hydrogenation catalyst, with stainless steel wool plugs at the top and bottom of the reactor. The reactor was jacketed and heated with a circulating oil. The reactor temperature was monitored by measuring the oil temperature, by means of an internal 0.05 cm (⅛") thermowell with an external 0.025 cm (1/16") slidable thermocouple to monitor peak temperature. The reactor temperature was controlled by adjustments in the oil temperature. An ISCO high pressure liquid metering pump was used to supply a mixed hydrogen/liquid feed to the reactor, with a mass flow controller being used to supply the hydrogen. The reactor outlet was attached to a condenser kept at 5 degrees Celsius by a chiller unit. The pressure within the reactor was controlled using a dome-loaded back pressure regulator. The catalyst was regenerated after reducing sugars in the product measured higher than 3%, using a water wash. Nickel loss by leaching was additionally monitored as a function of time.

For Example 1, hydrogen was supplied at 12.4 MPa (1800 psi), the liquid hourly space velocity was 1.0 hr$^{-1}$, and a reactor temperature of 115 degrees Celsius was used. The hydrogen to dextrose mass ratio was set at 20:1.

TABLE 1

Hydrogenation of 30% Dextrose Solution with time

| On stream hours | LHSV | Reducing Sugars, ppm | Reducing sugars, % | Ni, ppm | Dextrose conversion |
|---|---|---|---|---|---|
| 16 | 1 | 300 | 0.030 | 8.25 | 99.90% |
| 40 | 1 | 775 | 0.078 | 16.10 | 99.74% |
| 616 | 1 | 25,535 | 2.554 | 38.1 | 91.49% |
| 640 | 1 | 28,116 | 2.812 | 40.0 | 90.63% |
| Regeneration 1 | | | | | |
| 686 | 1 | 961 | 0.096 | 26.27 | 99.68% |
| 710 | 1 | 2,365 | 0.237 | 21.11 | 99.21% |
| 1838 | 1 | 12,888 | 1.289 | 7.94 | 95.70% |
| 1862 | 1 | 13,323 | 1.332 | 6.16 | 95.56% |
| Regeneration 2 | | | | | |
| 1886 | 1 | 1,273 | 0.127 | 5.27 | 99.58% |
| 2390 | 1 | 35,554 | 3.555 | 27.9 | 88.15% |
| 2414 | 1 | 36,573 | 3.657 | 23.3 | 87.81% |
| Regeneration 3 | | | | | |
| 2462 | 1 | 4,046 | 0.405 | 10.3 | 98.65% |
| 3230 | 1 | 25,088 | 2.509 | 12.5 | 91.64% |
| Regeneration 4 | | | | | |
| 3254 | 1 | 6,159 | 0.616 | 15.6 | 97.95% |
| 3854 | 1 | 23,756 | 2.376 | 3.71 | 92.08% |
| 3878 | 1 | 23,375 | 2.338 | 5.07 | 92.21% |
| Regeneration 5 | | | | | |
| 3902 | 1 | 3,389 | 0.339 | 8.49 | 98.87% |
| 4238 | 1 | 20,361 | 2.036 | 7.97 | 93.21% |

Table 1 shows the results from the first hydrogenation run. The 30% feed was processed for over 600 hours, then underwent regeneration. An initial loss of activity was recovered by a water washing process. The catalyst had 5 regenerations the catalyst bed was unloaded, after more than 4000 hrs run time. Productivity for the 30% solution hydrogenation over this time was 8.5 grams sorbitol per hour.

Example 2

Table 2 shows the results from hydrogenating the 20% dextrose feed in the same apparatus, by the same procedure and under the same conditions as in Example 1. The 20% feed was processed for over 6000 hours cumulative run time without deactivation or observed nickel leaching.

The average sorbitol production rate over the cumulative run time was lower with the dilution, however, at 5.9 g/hr for the 20% feed.

TABLE 2

Hydrogenation of 20% Dextrose Solution with time

| On stream hours | Reducing Sugars, ppm | Reducing sugars, % | Ni, ppm | Dextrose conversion |
|---|---|---|---|---|
| 202 | 8 | 0.0008 | 0 | 99.99% |
| 6200 | 10 | 0.001 | 0 | 99.99% |

Example 3

Table 3 shows results from hydrogenating a mixed aqueous solution of 20% dextrose with 20% sorbitol, in the same apparatus, by the same procedure and under the same conditions as used for Examples 1 and 2. The mixed feed was processed for over 1800 hours, again without deactivation or nickel leaching.

TABLE 3

Hydrogenation of 20% Mixed Solution with time

| On stream hours | Reducing Sugars, ppm | Reducing sugars, % | Ni, ppm | Dextrose conversion |
|---|---|---|---|---|
| 202 | 8 | 0.0008 | 0 | 99.99% |
| 1800 | 200 | 0.02 | 0 | 99.99% |

Example 4

Table 4 shows the results from hydrogenating a 20% dextrose feed at an LHSV of 1 hr$^{-1}$, with a single addition of a concentrated 55% dextrose solution with 0.25 ml/minute of additional hydrogen to obtain a net 19% dextrose concentration at the addition of the further dextrose solution and hydrogen in the reactor. The hydrogenation was continued over 2200 hours, without observed deactivation or nickel leaching. The average sorbitol production rate over this amount of runtime was 9.0 g/hr, substantially better than for the 20% single feed example and better even than the 30% single feed example, but with the reduced deactivation and nickel leaching performance of the 20% example.

TABLE 4

Hydrogenation of 20% Solution with Side Injection.

| On stream hours | Reactor 1 feed, Dextrose % | Reactor 2 feed, Dextrose % | Sorbitol at Outlet, wt % |
|---|---|---|---|
| 310 | 20 | 48 | 30.221 |
| 814 | 20 | 48 | 30.645 |
| 1174 | 20 | 48 | 30.453 |
| 1198 | 20 | 48 | 30.395 |
| 1700 | 20 | 48 | 30.505 |
| 2216 | 20 | 48 | 30.097 |
| 2240 | 20 | 48 | 30.493 |

Examples 5-10

A) Completion of Computer Model:

For modeling a continuous fixed-bed dextrose hydrogenation to sorbitol employing downstream additions according to the present invention, a 2.5 cm (1 inch) inner diameter, 180 cubic centimeter reactor was first procured and loaded with 288 grams of Raney® nickel sponge metal catalyst, then fed a 20 weight percent dextrose solution in water with hydrogen being supplied at a hydrogen/dextrose solution of 34:1 (LHSV of 1). The reactor was operated isothermally at 115 degrees Celsius and a pressure of 12.4 MPa (1800 psi). The sorbitol conversion at the outlet was 99.5 percent. No downstream addition of dextrose (or hydrogen with dextrose) was done.

The data gathered over a period of time from this experimental run was then used with the activation energy of 64.8 kJ/mol reported by Verma et al., "Kinetics of hydrogenation of D-glucose to sorbitol", J. Chem. Technol. Biotechnol. 1989, vol. 46, pp. 295-301, to determine the kinetic rate constant $k_r$ for use in a reaction rate equation, $$\text{rate}\left[\frac{\text{mol}}{\sec*\text{kg catalyst}}\right] = k_r\left[\frac{L^2}{\sec*\text{kg catalyst}*\text{mol}}\right]*\left(C_{Glucose}\left[\frac{\text{mol}}{L}\right]\right)*\left(C_{H_2}\left[\frac{\text{mol}}{L}\right]\right)$$

A model was subsequently constructed in ASPEN PLUS® process modeling and optimization software from Aspen Technology, Inc., Burlington, Mass. 01803, using the same conditions and a fixed exit conversion of 99.5%, to model the effects of different numbers of side injections and different injection positions. In regard to the latter variable, progressively greater amounts of the Raney® nickel sponge metal catalyst were observed to be required per each further unit of sorbitol produced, as the concentration of dextrose in solution decreased; it was postulated, then, that by staging downstream additions according to the concentration of dextrose in solution remaining unconverted at particular locations in the reactor, significant productivity improvements could be realized from the catalyst bed overall, by not permitting the unconverted dextrose concentration to fall to levels where the rate of production or sorbitol per unit of catalyst would begin to fall at higher rates.

Accordingly, as substantiated by the modeling that was done, the total catalyst requirements for production of a certain amount of sorbitol within a given timeframe from the modeled process could be minimized or at least significant reduced, or equivalent, for a given amount of catalyst, production of sorbitol could be significantly increased or even maximized for the modeled process by staging the selected number of downstream additions at certain positions along the axial flow of the reactor.

B) Results of Modeling Different Numbers of Side Stream Injections:

A series of dextrose to sorbitol hydrogenations were modeled in which no side stream injections were used (conventional case), a single side stream injection was used, then two and then three side stream injections were used. Fixed variables included the overall sorbitol production rate, the final temperature of each reactor bed section preceding a side stream injection and at the outlet (120 degrees Celsius), the inlet pressure of 12.4 MPa (1800 psi), the dextrose conversion of each reactor bed section (99.5%), the diameter of all reactor bed sections (same in all cases), the inlet hydrogen/dextrose molar ratio of 34:1, a targeted dextrose concentration of 20 percent and the use of more concentrated 50% dextrose solutions for each modeled addition.

Figure 3:
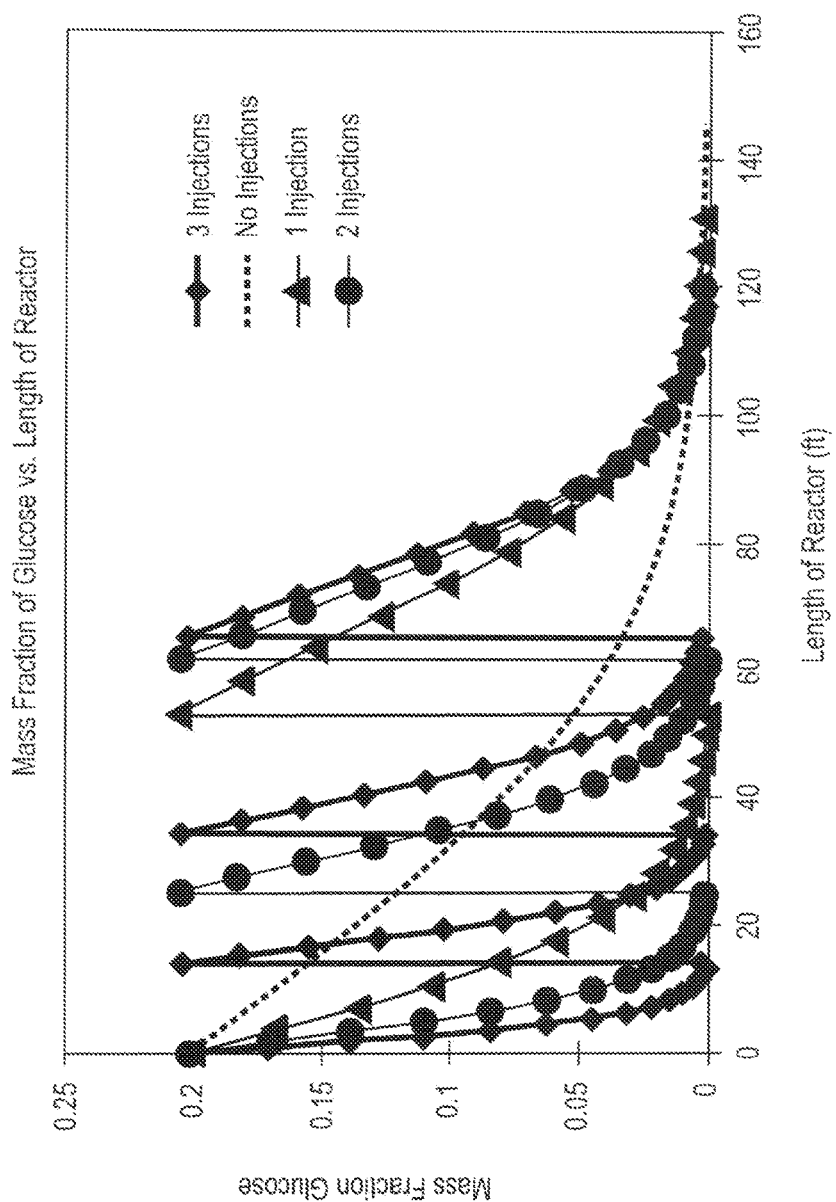
FIG. 3 shows the concentration profile of dextrose as a function of the number of side injections/downstream additions according to a process of the present invention, in a modeled continuous fixed bed process for producing sorbitol by the hydrogenation of an aqueous dextrose liquid phase reactant in the presence of a Raney® nickel sponge metal catalyst.

Table 5 demonstrates the results of using one, two or three side stream injections of 50% dextrose solution, where the total catalyst volume and average mass flow rate of the reactor bed sections are compared to a normalized value of 1.0 for the circumstance where no side stream injections are used in the model. In the "no side stream injection" case, sorbitol outlet concentration was 20.10 percent by weight. The increased sorbitol concentration realized through the use of side stream injections, it be appreciated, will be beneficial in terms of energy requirements for removing water from the sorbitol product. The data plotted in FIG. 3 also derive from the conditions and model results for the 0, 1, 2, and 3 injection cases; FIG. 3 further demonstrates how downstream additions provide dextrose concentrations in the reactor that are within thirty percent of the inlet concentration, for a greater portion of the reactor's length than in the no injection case, as well as that less catalyst volume is required where such downstream additions are made:

TABLE 5

| No. of Injections | 1 | 2 | 3 |
|---|---|---|---|
| Tot. Catalyst Volume | 0.903 | 0.826 | 0.794 |
| Avg. Mass Flow Rate of Beds | 0.489 | 0.329 | 0.250 |
| Sorbitol Concentration Out (% wt) | 32.62 | 39.73 | 43.86 |

C) Results of Modeling Three Staged Side Stream Injections According to Unconverted Dextrose Concentration Remaining in Solution:

Based on the results seen in Table 5 and to determine whether total catalyst requirements could be reduced by staging the side stream injections according to how much dextrose had been hydrogenated to sorbitol in a preceding reactor bed section, a series of simulations were done with the same reactor system and same fixed variables as modeled for Table 5. A first simulation made three additions of a 50% dextrose solution when 99.5% of the previously added dextrose had been converted, while a second simulation made its additions when 95% of the previously added dextrose had been converted and the third simulation made its additions when 70% had been converted. These results are shown in Table 6, with the results at the 99.5% conversion benchmark again being normalized to 1 for ease of comparison among the three cases:

TABLE 6

| Dextrose Conversion | 99.5% | 95% | 70% |
|---|---|---|---|
| Tot. Catalyst Volume | 1.0 | 0.805 | 0.701 |
| Avg. Mass Flow Rate of Beds | 1.0 | 1.039 | 1.351 |
| Sorbitol Concentration Out (% wt) | 43.86 | 43.36 | 39.58 |

What is claimed is:

1. A continuous process for hydrogenating a sugar in a feed of the sugar in water to a corresponding sugar alcohol and for managing the concentrations of hydrogen and of the sugar to be hydrogenated thereby along the length of a continuous reactor from its first inlet to its outlet without recycling and without introducing a diluent in any portion of the reaction mixture, comprising providing the continuous reactor containing a nickel sponge metal catalyst and having a plurality of inlets and introducing the feed and hydrogen into the reactor to react in the presence of the catalyst, with the feed being introduced at a targeted concentration of the sugar in water of not more than about 30 percent by weight at the first inlet and at one or more downstream inlet locations along the reactor in the axial direction of fluid flow.

2. A continuous process for hydrogenating a sugar in a feed of the sugar in water to a corresponding sugar alcohol and for managing the concentrations of hydrogen and of the sugar to be hydrogenated thereby along the length of a continuous reactor from its first inlet to its outlet without recycling and without introducing a diluent in any portion of the reaction mixture, comprising providing the continuous reactor containing a nickel sponge metal catalyst and having a plurality of inlets and introducing the feed and hydrogen into the reactor to react in the presence of the catalyst, with the feed being introduced at the first inlet at a targeted concentration of the sugar in water of not more than about 30 percent by weight, and then introducing the sugar into the reactor at a selected number and placement of downstream inlet locations in the axial direction of fluid flow in the form of an aqueous solution at a concentration or in the form of a plurality of aqueous solutions at sugar concentrations greater than the targeted concentration at the first inlet, provided that the one or more downstream introductions do not result in a concentration of the sugar within the reactor that exceeds the targeted concentration by more than thirty percent.

3. The process according to either of claim 1 or claim 2, wherein the effect of the one or more downstream introductions is to achieve a concentration of the sugar within the reactor that is within thirty percent of the targeted concentration value at the first inlet over at least about ten percent of the length of a catalyst bed.

4. The process according to claim 3, wherein the concentration of the sugar is within thirty percent or the targeted concentration value at the first inlet over at least about thirty percent of the length of a catalyst bed.

5. The process according to either of claims 1 or 2, further comprising introducing the hydrogen into the reactor at one or more downstream inlet locations.

6. The process according to either of claims 1 or 2, further comprising selecting the number of downstream introductions of the sugar as well as the downstream inlet locations for these introductions to provide at least a ten percent reduction in the total volume of nickel sponge metal catalyst that is required to produce the corresponding sugar alcohol at a given rate of production, compared to the volume of the same nickel sponge metal catalyst that is required under the same conditions but in the absence of any downstream introductions of the sugar.

7. The process according to claim 6, wherein at least a twenty percent reduction is realized in the total volume of catalyst required.

8. The process according to claim 7, wherein at least a thirty percent reduction is realized in the total volume of catalyst required.

9. The process according to claim 1, wherein the sugar in water is an aqueous dextrose solution, and the dextrose is continuously hydrogenated to produce sorbitol.

10. The process according to claim 9, wherein the catalyst is a Raney® nickel sponge metal catalyst and the targeted dextrose concentration at the first inlet is selected in the range of from 20 to 30 percent by weight.

11. The process according to claim 10, wherein the targeted dextrose concentration at the first inlet is selected in the range of from 20 to 25 percent by weight.

12. The process according to claim 11, wherein the targeted dextrose concentration at the first inlet is 20 percent by weight.

13. A process for continuously producing sorbitol, comprising:
continuously supplying hydrogen and an aqueous dextrose feed at a concentration of not more than about 30 percent by weight to a first inlet of a reactor containing a nickel sponge metal catalyst; and
continuously introducing additional supplies of the aqueous dextrose feed into the reactor at a selected number and placement of two or more downstream inlet locations from the first inlet, in each instance where at least 99.5 percent of the dextrose previously added has been reacted.

14. The process according to claim 13, wherein the concentration to the first inlet is from 20 to 30 percent by weight.

15. The process according to claim 14, wherein the concentration to the first inlet is from 20 to 25 percent by weight.

16. The process according to claim 15, wherein the concentration to the first inlet is 20 percent by weight.

17. A process for continuously producing sorbitol, comprising:
continuously supplying hydrogen and an aqueous dextrose feed at a concentration of not more than about 30 percent by weight to a first inlet of a reactor containing a nickel sponge metal catalyst; and
continuously introducing additional supplies of the aqueous dextrose feed into the reactor at a selected number and placement of three or more downstream inlet locations from the first inlet, in each instance where at least 70 percent of the dextrose previously added has been reacted.

18. The process according to claim 17, wherein the concentration at the first inlet is from 20 to 30 percent by weight.

19. The process according to claim 18, wherein the concentration at the first inlet is from 20 to 25 percent by weight.

20. The process according to claim 19, wherein the concentration at the first inlet is 20 percent by weight.

* * * * *